United States Patent
Kihara et al.

(10) Patent No.: US 11,589,977 B2
(45) Date of Patent: Feb. 28, 2023

(54) KIT FOR PREPARING A CUSTOMIZABLE FLESH SIMULATING SILICONE GEL OR SILICONE FOAM IN PARTICULAR FOR USE IN MEDICAL DEVICES

(71) Applicants: Elkem Silicones USA Corp., East Brunswick, NJ (US); Elkem Silicones Germany GmbH, Luebeck (DE)

(72) Inventors: Matthew Kihara, Dublin, CA (US); Francois Martin, Luebeck (DE); Matthew Ryan, Rock Hill, SC (US); Yan Meng, Rock Hill, SC (US); Leeanne Brown, Chester, SC (US)

(73) Assignees: ELKEM SILICONES USA CORP., East Brunswick, NJ (US); ELKEM SILICONES GERMANY GMBH, Lubeck (DE)

( * ) Notice: Subject to any disclaimer, the term of this patent is extended or adjusted under 35 U.S.C. 154(b) by 692 days.

(21) Appl. No.: 16/588,338

(22) Filed: Sep. 30, 2019

(65) Prior Publication Data

US 2020/0100893 A1  Apr. 2, 2020

Related U.S. Application Data

(60) Provisional application No. 62/740,123, filed on Oct. 2, 2018.

(51) Int. Cl.
| | |
|---|---|
| *A61F 2/12* | (2006.01) |
| *A61L 27/18* | (2006.01) |
| *A61L 27/56* | (2006.01) |
| *C08J 9/06* | (2006.01) |
| *A61L 27/00* | (2006.01) |
| *B33Y 10/00* | (2015.01) |
| *B33Y 70/00* | (2020.01) |
| *B33Y 80/00* | (2015.01) |

(52) U.S. Cl.
CPC ............ *A61F 2/12* (2013.01); *A61L 27/00* (2013.01); *A61L 27/18* (2013.01); *A61L 27/56* (2013.01); *C08J 9/06* (2013.01); *A61F 2240/002* (2013.01); *A61L 2430/04* (2013.01); *B33Y 10/00* (2014.12); *B33Y 70/00* (2014.12); *B33Y 80/00* (2014.12); *C08J 2207/10* (2013.01); *C08J 2383/04* (2013.01)

(58) Field of Classification Search
CPC ....................................................... A61F 2/12
See application file for complete search history.

(56) References Cited

U.S. PATENT DOCUMENTS

| | | |
|---|---|---|
| 3,159,601 A | 12/1964 | Ashby |
| 3,159,602 A | 12/1964 | Hamilton et al. |
| 3,188,299 A | 6/1965 | Chalk |
| 3,220,972 A | 11/1965 | Lamoreaux |
| 3,377,432 A | 4/1968 | Abbott et al. |
| 3,419,593 A | 12/1968 | Willing |
| 3,498,945 A | 3/1970 | Lefort et al. |
| 3,715,334 A | 2/1973 | Karstedt |
| 3,775,452 A | 11/1973 | Karstedt |
| 3,814,730 A | 6/1974 | Karstedt |
| 3,923,705 A | 12/1975 | Smith |
| 3,989,667 A | 11/1976 | Lee et al. |
| 4,256,870 A | 3/1981 | Eckberg |
| 4,347,346 A | 8/1982 | Eckberg |
| 5,009,957 A | 4/1991 | Lee et al. |
| 2013/0310781 A1* | 11/2013 | Phillips ............... A61L 15/585 521/134 |

FOREIGN PATENT DOCUMENTS

| | | | |
|---|---|---|---|
| EP | 0057459 A1 | 8/1982 | |
| EP | 0188978 A1 | 7/1986 | |
| EP | 0190530 A1 | 8/1986 | |
| EP | 751173 A1 * | 1/1997 | ............... C08J 9/08 |
| FR | 2856072 A1 | 12/2004 | |
| FR | 2913688 A1 | 9/2008 | |
| WO | 2016205468 A1 | 12/2016 | |
| WO | 2017144461 A1 | 8/2017 | |

OTHER PUBLICATIONS

English machine translation of Berger et al. (EP 0 751 173). (Year: 1997).*
International Search Report for PCT/US2019/053851, dated Jan. 28, 2020.

* cited by examiner

*Primary Examiner* — Michael F Pepitone
(74) *Attorney, Agent, or Firm* — McBee Moore & Vanik IP, LLC

(57) ABSTRACT

The present invention relates to a kit for preparing a customizable flesh simulating silicone gel or a flesh simulating silicone foam in particular for use in medical devices and a process for preparing said customizable flesh simulating silicone gel or silicone foam, in particular by using a 3D-printer.

17 Claims, No Drawings

KIT FOR PREPARING A CUSTOMIZABLE FLESH SIMULATING SILICONE GEL OR SILICONE FOAM IN PARTICULAR FOR USE IN MEDICAL DEVICES

CROSS-REFERENCE TO RELATED APPLICATIONS

This patent application claims the benefit of U.S. Provisional Application No. 62/740,123, filed on 2 Oct. 2018, the contents of which are hereby incorporated by reference in its entirety.

BACKGROUND

The present invention relates to a kit for preparing a customizable flesh simulating silicone gel or a customizable flesh simulating silicone foam, in particular for use in medical devices and a process for manufacturing them. In addition, the present invention relates to a breast implant comprising said specific silicone gels and foams which are used as fillings. It also relates to a new process for additive manufacturing a 3D-shape article and to new 3D-shape articles made of said customizable flesh simulating silicone gel or silicone foam which can be useful as medical implant.

Nowadays, reconstructive and cosmetic surgery has become a common practice as almost any part of the body can be filled to create balance and harmony. For reconstructive and cosmetic surgery, an implant is used. The use of implants is forecast to a high increase due to the population aging, boost in life expectancy and style of life and improvements in implant technology. The term "implant" in this patent application means a medical device manufactured to replace a missing biological structure, support a damaged biological structure, or enhance an existing biological structure.

The implant is required to be able to provide a specific three-dimensional shape and maintain the shape for a certain period depending on the nature of the implant. The implant also needs to be bio-durable such that it is not damage by interaction with the human body; and it needs to be biocompatible. The biocompatibility of a mid-term or long-term implantable medical device refers to its ability to perform its intended function without creating any undesirable local or generalized effects.

For some specific implant applications, it is also needed that the implant is made of a material that has adequate resilience property so that the implant could mimics a real human tissue at the position of the implant. Resilience is an indicator of a material's ability to absorb energy without undergoing permanent deformation.

Furthermore, it is not the only required property for such implants as there is also a strong demand for implants to have a specific feel imitating the feel of human tissue. Indeed, patients who need medical devices are necessitating ever-more custom solutions to improve the sensory feel of the implanted material to match the feel of their natural flesh. Custom sensory materials will improve the quality of life for patients who need devices implanted and improve the emotional and social acceptance of such devices.

Most implants used in plastic surgery are composed of a silicone-based material which have long been recognized as one of, if not the most, biocompatible synthetic material in existence. Whereas among all types of cosmetic and reconstructive implants, the breast implant had the largest number of implementation. Reconstructive breast surgery is practiced allowing reconstruction of a woman's breast that was affected by mastectomy whereas cosmetic breast surgery is practiced to amend the appearance of a woman's breast, for example by adding an implant to increase the size of the breast, to correct asymmetries, change shape and fix deformities.

However, implants are now used more and more for other facial implants, such as brow, nose, cheek, chin and lips, and various body implants, such as tracheal stents, implantable adipose enhancements or replacements, such as gluteus maximus, breast or cheek implants; or firmer tissues such as a calf, bicep, tricep, or abdominal muscles.

Furthermore, customization of medical implants is now even more accessible with the development of three-dimensional (3D) printing, which is more formally referred to as additive manufacturing (AM). Additive manufacturing (AM) consists of creating a three-dimensional object layer by layer using computer-aided design (CAD). 3D printing is providing effective solutions and show great potential for personalized medicine and care. Indeed, due to the increasing demand for tissue and organ transplantation, and the deficiency of tissue and organ donors, numerous efforts have been made to develop biological substitutes for native human tissues and organs. 3D printing is also used to fabricate customized scaffolds with controlled pore size and pore structure which are used for tissue engineering, as the 3D-printed construct acts as a growth-directing structure on which cells for witch sufficient nutrients are supplied could migrate and proliferate into these 3D scaffolds to form a functional tissue once implanted.

As the medical field is moving towards customization of implants, it is still in need of a biocompatible material for which sensory feel properties could be easily customized to each patient for use in medical devices such as implants. Custom sensory of said biocompatible material will improve the quality of life for patients who need devices implanted and improve the emotional and social acceptance of such devices. In particular, improvement of fillings used in breast implants would benefit from such biocompatible material.

It is also needed a convenient process for manufacturing such biocompatible material to allow customization of the sensory feel properties of such biocompatible material. In particular, said biocompatible material should have adequate resilience property so that the implant could mimics a real human tissue at the position of the implant There is also a strong need to provide an additive manufacturing method for the efficient production of such biocompatible material.

SUMMARY

In this context, one of the essential objectives of the present invention is to provide a new kit for preparing a customizable flesh simulating silicone gel or a customizable flesh simulating silicone foam which will have the advantage of having low density properties.

Another essential objective of the invention is to provide a new process for preparing such customizable flesh simulating silicone gel or customizable flesh simulating silicone foam.

Another essential objective of the invention is to provide a breast implant comprising said specific silicone gels or silicone foams which are used as fillings.

Another essential objective of the invention is to provide a new process for additive manufacturing a 3D-shape article made of said customizable flesh simulating silicone gel or said customizable flesh simulating silicone foam. Such process will also enable to manufacture complex shape objects made of such biocompatible materials.

Another essential objective of the invention is to provide a 3D-shape article made of said customizable flesh simulating silicone gel or said customizable flesh simulating silicone foam.

DETAILED DESCRIPTION

All these objectives, among others, are achieved by the present invention, which relates to a kit for preparing a customizable flesh simulating silicone gel in particular for use in medical devices comprising:
a first package Part-A comprising a mixture of:
  i) 5 to 95 parts by weight of at least one organopolysiloxane A1 having at least two alkenyl groups bonded to silicon per molecule, said alkenyl groups each containing from 2 to 14 carbon atoms, preferably said alkenyl groups are chosen from the group consisting of vinyl, allyl, hexenyl, decenyl and tetradecenyl, and most preferably said alkenyl groups are vinyl groups, and
  ii) at least one hydrosilylation catalyst C1;
a second package Part-B comprising a mixture of:
  i) 95 to 5 parts by weight of at least one organopolysiloxane A2 having at least two alkenyl groups bonded to silicon per molecule, said alkenyl groups each containing from 2 to 14 carbon atoms, preferably said alkenyl groups are chosen from the group consisting of vinyl, allyl, hexenyl, decenyl and tetradecenyl, and most preferably said alkenyl groups are vinyl groups,
  ii) at least one organosilicon compound B1 having at least two and preferably at least three hydrogen atoms bonded to silicon per molecule,
  iii) eventually at least one diorganohydrogensiloxy-terminated polyorganosiloxane as a chain extender B2 and
  iii) eventually a cure rate controller G1 which slows the curing rate, and
a third package Part-C comprising:
  i) at least one linear polydimethylsiloxane D1 which has a dynamic viscosity at 25° C. of between 50 mPa·s and 100000 mPa·s, preferably of between 50 mPa·s to 70000 mPa·s,
  ii) eventually at least one organopolysiloxane A1 or A2, and
  iii) eventually at least one additive H1 such as a pigment, an antimicrobial agent or a rheology modifier,
with the proviso that:
a) the amounts of components A1 and A2 is 100 parts by weight when the contents of the three packages Part-A, Part-B and Part-C are combined,
b) the components B1 and B2 are present in an amount such that the molar ratio of silicon-bonded hydrogen atoms contained in components B1 and B2 to alkenyl groups contained in components A1 and A2 ranges from 0.25 to 0.90;
c) the amount of component D1 is at least about 0.1 part by weight percent to about 90 parts by weight for each 100 parts of the combined components A1 and A2 when the contents of the three packages Part-A, Part-B and Part-C are combined, and d) the component A1 is present in an amount sufficient to cure the composition formed when the contents of the three packages Part-A, Part-B and Part-C are combined.

To achieve this objective, the Applicant demonstrated, to its credit, entirely surprisingly and unexpectedly, that by providing a multi-part kit intended to be combined to prepare a silicone gel in which the ingredients are carefully placed, do address the need of providing to manufacturers a ready-to-use kit that will allow them to prepare a silicone gel for which sensory feel properties could be easily customized. This is made possible by providing in said multi-part kit, a specific part-C comprising a specific linear polydimethylsiloxane D1 that can be used by simply varying its amount added and/or its viscosity within the range according to the invention when all the three parts are combined. As it is known that designing a device with a biocompatible material with sensory feel properties that could be easily customized is challenging, this kit opens a new route for customization of medical implant especially in 3D-printing area. Hence, it will help to improve the quality of life for patients who need devices implanted and improve the emotional and social acceptance of such devices.

All the viscosities under consideration in the present specification correspond to a dynamic viscosity magnitude that is measured, in a manner known per se, at 25° C., at a sufficiently low shear rate gradient so that the viscosity measured with a machine of Brookfield type is independent of the rate gradient.

According to a first embodiment of the invention said linear polydimethylsiloxane D1 has the following formula:

$(CH_3)_3SiO(SiO(CH_3)_2)nSi(CH_3)$ in which n is an integer from 50 to 900, and preferably from 50 to 700.

According to another preferred embodiment, the kit according to the invention further contains a fourth package part-D comprising:
  at least one blowing agent E1, and preferably said blowing agent E1 is a chemical blowing agent, and most preferably said blowing agent E1 is chosen from the group consisting of ammonium bicarbonate, ammonium hydrogen carbonate, alkali metal hydrogen carbonate and mixtures thereof, and
  eventually at least one organopolysiloxane A1 or A2 which are defined according to the invention in Part-A and Part-B.

According to another preferred embodiment, the third package Part-C further comprise at least one blowing agent E1. Said blowing agent E1 could be any liquids or solids that generate gas by chemical decomposition or evaporation which are well known by the man of the art.

Preferably said blowing agent E1 is a chemical blowing agent, and most preferably said blowing agent E1 is chosen from the group consisting of ammonium bicarbonate, ammonium hydrogen carbonate, alkali metal hydrogen carbonate and mixtures thereof.

For the ease of application and production, the blowing agent E1 can be pre-dispersed in said organopolysiloxane A1, for example at a level from 30% to 60% by weight, with an eventual incorporation of any additive that could help to stabilize the shelf-life of the resulting composition.

In another preferred embodiment, the blowing agent E1 is chosen from the group consisting of ammonium bicarbonate, ammonium hydrogen carbonate, alkali metal hydrogen carbonate and mixtures thereof and wherein said blowing agent E1 has particles having a median particle size (D50) of ≤50 μm, and even more preferably ≤10 μm.

Examples of suitable organopolysiloxanes A1 and A2 according to the invention are polymers of the following formula:

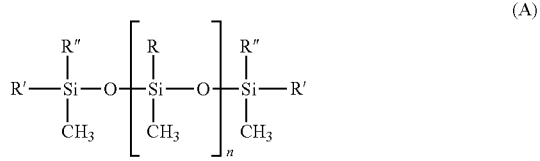

(A)

in which:
R and R", are chosen independently of one another from the group consisting of $C_1$ to $C_{30}$ hydrocarbon radical, and preferably R and R are an alkyl group chosen from the group consisting of methyl, ethyl, propyl, trifluoropropyl, and phenyl, and most preferably R is a methyl group, R' is a C1 to C20 alkenyl radical, and preferably R' is chosen from the group consisting of vinyl, allyl, hexenyl, decenyl and tetradecenyl, and most preferably R' is a vinyl radical, and n is an integer having a value from 5 to 1000, and preferably from 100 to 600.

As other examples of organopolysiloxane A1 or A2 that are of use, mention may be made of:
polydimethylsiloxanes comprising dimethylvinylsilyl end groups;
poly(methylphenylsiloxane-co-dimethylsiloxane) comprising dimethylvinylsilyl end groups; and
poly(vinylmethylsiloxane-co-dimethylsiloxane) comprising dimethylvinylsilyl end groups;

Examples of hydrosilylation catalysts A1 are hydrosilylation catalysts such as Karstedt's catalyst shown in U.S. Pat. No. 3,715,334 or other platinum or rhodium catalysts known to those in the art, and also including microencapsulated hydrosilylation catalysts for example those known in the art such as seen in U.S. Pat. No. 5,009,957. However, hydrosilylation catalysts pertinent to this invention can contain at least one of the following elements: Pt, Rh, Ru, Pd, Ni, e.g. Raney Nickel, and their combinations. The catalyst is optionally coupled to an inert or active support. Examples of preferred catalysts which can be used include platinum type catalysts such as chloroplatinic acid, alcohol solutions of chloroplatinic acid, complexes of platinum and olefins, complexes of platinum and 1,3-divinyl-1,1,3,3-tetramethyldisiloxane (known as Karstedt catalyst) and powders on which platinum is supported, etc. The platinum catalysts are fully described in the literature. Mention may in particular be made of the complexes of platinum and of an organic product described in U.S. Pat. Nos. 3,159,601, 3,159,602 and 3,220,972 and European Patents EP-A-057, 459, EP-188,978 and EP-A-190,530 and the complexes of platinum and of vinylated organopolysiloxane described in U.S. Pat. Nos. 3,419,593, 3,715,334, 3,377,432, 3,814,730, and 3,775,452. In particular, platinum type catalysts are especially desirable. The platinum catalyst ought preferably to be used in a catalytically sufficient amount, to allow sufficiently rapid crosslinking at room temperature. Typically, 1 to 200 ppm by weight of the catalyst are used, based in the amount of Pt metal, relative to the total silicone composition when the contents of Part-A, Part-B and Part-C are combined, preferably 1 to 100 ppm by weight, more preferably 1 to 50 ppm by weight.

In a preferred embodiment, said organosilicon compound B1 is an organopolysiloxane comprising:
at least three siloxy units of formula (XL-1):

(XL-1)

in which the symbol H represents a hydrogen atom, the symbol L represents an alkyl having from 1 to 8 carbon atoms inclusive or a C6 to $C_{10}$ aryl, and the symbol e is equal to 0, 1 or 2; and
optionally other siloxy units of formula (XL-2):

(XL-2)

in which the symbol L represents an alkyl having from 1 to 8 carbon atoms inclusive or a C6 to $C_{10}$ aryl and the symbol g is equal to 0, 1, 2 or 3.

The organopolysiloxane compound B1 may be formed solely from siloxyl units of formula (XL-1) or may also comprise units of formula (XL-2). It may have a linear, branched or cyclic structure. The degree of polymerization is preferably greater than or equal to 2. More generally, it is less than 1000. Its dynamic viscosity is usually ranging from about 1 to 2000 mPa·s at 25° C., generally from about 5 to 2000 mPa·s at 25° C., or preferably from 5 to 500 mPa·s at 25° C.

As examples of diorganohydrogensiloxy-terminated polyorganosiloxane as a chain extender B2, mention may be made of polydimethylsiloxanes comprising dimethyl hydrogensiloxy end groups having a dynamic viscosity at 25° C. of between 1 mPa·s and 500 mPa·s, preferably of between 5 mPa·s and 200 mPa·s, even more preferentially of between 1 and 30 mPa·s.

Particularly advantageous chain extender B2 are poly(dimethylsiloxy)-α,ω-(dimethyl hydrogensiloxy) of formula $M^H D_x M^H$ in which:
$M^H$=siloxyl unit of formula: $(H)(CH_3)_2SiO_{1/2}$
D=siloxyl unit of formula: $(CH_3)_2SiO_{2/2}$, and
x is an integer between 1 and 200, preferably between 1 and 150 and even more preferentially between 3 and 120.

The chain extender B2 is described as "chain extender" since it has the presumed effect of increasing the mesh size of the network when it is crosslinked. When the SiH reactive functions are at the chain end, the term "telechelic" polymer is sometimes used.

Examples of cure rate controller G1, which are also known as catalyst inhibitor, are designed to slow the cure of the compounded silicone if needed. Cure rate controllers are well known in the art and examples of such materials can be found in U.S. Patents. U.S. Pat. No. 3,923,705 refers to the use of vinyl contained cyclic siloxanes. U.S. Pat. No. 3,445,420 describes the use of acetylenic alcohols. U.S. Pat. No. 3,188,299 shows the effectiveness of heterocyclic amines. U.S. Pat. No. 4,256,870 describes alkyl maleates used to control cure. Olefinic siloxanes can also be used as described in U.S. Pat. No. 3,989,667. Polydiorganosiloxanes containing vinyl radicals have also been used and this art can be seen in U.S. Pat. Nos. 3.498,945, 4,256,870, and 4,347, 346. Preferred inhibitors for this composition are methylvinylcyclosiloxanes, 3-methyl-1-butyn-3-ol, and 1-ethynyl-1-cyclohexanol with the most preferred being the 1,3,5,7-tetramethyl-1,3,5,7-tetravinyl-cyclotetrasiloxane in amounts from 0.002% to 1.00% of the silicone compound depending on the cure rate desired. The preferred cure rate controller G1 is chosen among:

1,3,5,7-tetramethyl-1,3,5,7-tetravinyl-cyclotetrasiloxane.
3-methyl-1-butyn-3-ol, and
1-ethynyl-1-cyclohexanol.

To obtain a longer working time or "pot life", the quantity of the cure rate controller G1 is adjusted to reach the desired "pot life". The concentration of the catalyst inhibitor in the present silicone composition is sufficient to retard curing of the composition at ambient temperature without preventing or excessively prolonging cure at elevated temperatures. This concentration will vary widely depending on the particular inhibitor used, the nature and concentration of the hydrosilylation catalyst, and the nature of the organohydrogenopolysiloxane. Inhibitor concentrations as low as one mole of inhibitor per mole of platinum group metal will in some instances yield a satisfactory storage stability and cure rate. In other instances, inhibitor concentrations of up to 500 or more moles of inhibitor per mole of platinum group metal may be required. The optimum concentration for a particular inhibitor in a given silicone composition can be readily determined by routine experimentation. Advantageously, the amount of the cure rate controller G1 in the addition-crosslinking silicone compositions is in the range from 0.01% to 0.2% weight, preferably from 0.03% to 0.15% weight with respect to the total weight of the silicone composition when the contents of Part-A, Part-B and Part-C are combined.

In a preferred embodiment:
the organopolysiloxanes A1 and A2 have a dynamic viscosity at 25° C. of between 100 mPa·s and 120 000 mPa·s, and preferably of between 5000 mPa·s and 20000 mPa·s,
the chain extender B2 has a dynamic viscosity at 25° C. of between 1 mPa·s and 500 mPa·s, and preferably between 5 and 200 mPa·s, and
the said organosilicon compound B1 has a dynamic viscosity at 25° C. of between 5 mPa·s and 2000 mPa·s, and preferably between 5 and 500 mPa·s.

In an advantageous embodiment of the invention, the packages Part-A, Part-B and/or Part-C further comprise at least one thixotropic agent F1. Any thixotropic agent suitable for silicone compositions which crosslink via addition reactions could be used. Indeed, especially in the field of 3D-printing, it is advantageous for the composition formed when the ingredients of Part-A, Part-B and Part-C are combined to have the adequate rheological properties to avoid collapse or deformation of the objects or drops at room temperature before the curing is complete. When such additive is present within the kit according to the invention, the resulting composition could possess thixotropic behavior so that when it is extruded out smoothly and after the extrusion, the drop or object will still retain its shape allowing sufficient time to allow the crosslinking reaction to occur.

In a preferred embodiment, said thixotropic agent F1 is an organopolysiloxane-polyoxyalkylene copolymer. Organopolysiloxane-polyoxyalkylene copolymer, also known as polydiorganosiloxane-polyether copolymers or polyalkylene oxide modified polymethylsiloxane, are organopolysiloxanes containing siloxyl units which carry alkylene oxide chain sequences. Preferably, suitable organopolysiloxane-polyoxyalkylene copolymer are organopolysiloxanes containing siloxyl units which carry ethylene oxide chain sequences and/or propylene oxide chain sequences. An example of organopolysiloxane-polyoxyalkylene copolymer that can be used corresponds to the formula (E-2):

$R^a{}_3SiO[R^aSiO]_t[R^aSi(R^b\text{-}(OCH_2CH_2)_x(OCH_2CH_2CH_2)_y\text{-}H)O]_rSiR^a{}_3$ (E-2)

in which:
each $R^a$ is independently selected from alkyl groups containing from 1 to 8 carbon atoms and preferably $R^a$ is a methyl group,
each $R^b$ is a divalent hydrocarbon group having from 2 to 6 carbon atoms or a direct bond, and preferably $R^b$ is a propyl group,
x and y are independently integers comprised from 1 to 40, preferably from 5 and 30, and most preferably from 10 to 30,
t is comprised from 1 to 200, preferably from 25 to 150, and
r is comprised from 2 to 25, preferably from 3 to 15.

Advantageously, in an embodiment the thixotropic agent F1 is:

Me3SiO[Me$_2$SiO]$_{75}$[MeSi((CH$_2$)$_3$—(OCH$_2$CH$_2$)$_{22}$(OCH$_2$CH(CH$_3$))$_{22}$—OH)O]$_7$SiMe$_3$.

Methods of preparing polydiorganosiloxane-polyoxyalkylene copolymers are well known in the art. For example, a polydiorganosiloxane-polyoxyalkylene copolymer can be prepared using a hydrosilylation reaction by reacting, for example, a polydiorganosiloxane containing silicon-bonded hydrogen atoms with a polyoxyalkylene containing groups having aliphatic unsaturation in the presence of a platinum group catalyst. The amount of organopolysiloxane-polyoxyalkylene copolymer in the addition-crosslinking silicone compositions when present is at least 0.3% weight, preferably at least 0.4% weight, most preferably in the range from 0.6% to 4% weight, and even most preferably from 0.6% to 3% weight with respect to the total weight of the silicone composition when the contents of Part-A, Part-B and Part-C are combined.

Examples of suitable additives H1 includes: a resilient additive, a filler; a silicone resin, a pigment; an antimicrobial agent, a radio opaque additive; a UV stabilizer; a fragrance; a flavor; an essential oil; a flame resistant additive; a thermal stabilizer; a rheology modifier; a thickener; an adhesion promoter; a biocide; a preservative; an enzyme; a peptide; a surface-active agent; a reactive diluent; a pharmaceutical active; an excipient or a cosmetic ingredient.

Adhesion promoters are largely used in silicone composition. Advantageously, it is possible to use one or more adhesion promoter(s) chosen in the group consisting of:
alkoxylated organosilanes comprising, per molecule, at least one $C_2$-$C_6$ alkenyl group,
organosilicate compounds comprising at least an epoxy radical, and
chelates of metal M and/or metallic alkoxydes of formula:

$M(OJ)_n$ in which:
M is chosen in the group consisting of: Ti, Zr, Ge, Li, Mn, Fe, Al and Mg or their mixtures, preferably M is chosen in the group consisting of: Ti, Zr, Ge, Li or Mn, and more preferably M is titanium, and
n=valence of M and J=linear or branched alkyl in $C_1$-$C_8$.

Silicon resins are branched organopolysiloxanes well known and commercially available. They present, in their structure, at least two different units chosen among those of formula: $R_3SiO_{1/2}$ (M unit), $R_2SiO_{2/2}$ (D unit), $RSiO_{3/2}$ (T unit) and $SiO_{4/2}$ (Q unit), at least one of these units being a T or Q unit. In said formulas, radicals R are identical or different and chosen in the group consisting of alkyl linear or branched in $C_1$-$C_6$, hydroxyl, phenyl, trifluoro-3,3,3 propyl. Alkyl radicals are for example methyl, ethyl, isopropyl, tertiobutyl and n-hexyl. As examples of branched oligomers or organopolysiloxanes polymers, there can be cited MQ resins, MDQ resins, TD resins and MDT resins, which can have hydroxyl functions that can be carried by M, D and/or T units. As examples of resins that are particularly well suited, there can be cited hydroxylated MDQ resin having from 0.2 to 10% by weight of hydroxyl group.

The antimicrobial agent can include chlorhexidine digluconate, elemental copper, elemental silver, silver salts, a copper-containing compound, a silver-containing compound, or a combination thereof.

Another object of the invention concerns a process for preparing a customizable flesh simulating silicone gel or a customizable flesh simulating silicone foam in particular for use in medical devices comprising the steps of:
a) combining the contents or portions of the three packages Part-A, Part-B and Part-C, and eventually Part-D, according to the invention and as defined above to yield a crosslinkable silicone composition X precursor of a silicone gel or a silicone foam, and
b) allowing the said crosslinkable silicone composition X to crosslink, to yield a customizable flesh simulating silicone gel or a customizable flesh simulating silicone foam, and
wherein the sensory flesh-feel properties of the resulting silicone gel or the silicone foam are customized in step a) by metering and adding the required amounts of the contents of Part-C corresponding to the required level of sensory flesh-feel properties of the customizable flesh simulating silicone gel or of the customizable flesh simulating silicone foam.

As stated above this new process do address the need of providing to manufacturers a process that will allow them to prepare a silicone gel or a silicone foam for which sensory feel properties could be easily customized.

Metering can be done by any means, for example by weight (using a balance) or by volume (measuring vessel, pipette or disposable syringe). If the amounts are relatively large, in step a) of the process according to the invention, a mechanical stirrer or an automatic mixing and metering system can be used. Suitable mixing tools are paddle stirrers with perforated, inclined blades. High-speed stirrers using toothed discs (dissolvers) are also suitable. For processing large quantities of shear thinning/thixotropic compositions, automatic dosing equipment, can be run with either static mixers or dynamic mixing heads. Fully automated processing mixing apparatus can be used such that in step a) of the process according to the invention, ingredients of Part-A, Part-B and Part-C, and of Part-D when present, for example conditioned in the form of pails or drums, are pumped by metering units (e.g., gear pump or helical pump) in the desired ratio directly from the pails or drums and feed them to the mixing unit, which can be either a static or a dynamic mixer. This can also be supported by additional gear pumps, helical pumps or volumetric piston systems. A suitable mixer is chosen, depending on the rheological properties and the flow rate of the crosslinkable silicone composition X. Indeed, static mixers do not have moving parts, and the composition is homogenized via fixed mixing elements on the interior whereas dynamic mixers support homogenization with moving parts.

The curing of said crosslinkable silicone composition X in step b) of the process according to the invention can be easily obtained without the need of heat, so at ambient temperature 20° C. (+/−5° C.), by adjusting the level of inhibitor and/or catalyst. However, it can also be greatly accelerated by heat curing at a temperature range of between 80° C. to 200° C., preferably of between 100° C. to 185° C.

Another object of the invention concerns a customizable flesh simulating silicone gel or a customizable flesh simulating silicone foam obtained according process of the invention described above.

Another object of the invention concerns a breast implant comprising a shell and a filling enclosed by a shell wherein the filling is the customizable flesh simulating silicone gel or the customizable flesh simulating silicone foam according to the invention and as described above.

The shell may therefore be for instance a silicone elastomer, preferably a vulcanized silicone rubber, which can be single or multi layered, smooth or textured, barrier-coated, or covered with polyurethane foam. Conventional breast implant shells are multilayered or laminated. Specifically, such shells include outer "rupture-resistant" layers, and an inner "barrier" layer, sandwiched between the outer layers and effective to resist gel bleed. For example, it can include a low diffusion silicone elastomer shell made with outer layers of a dimethyl-diphenyl silicone elastomer, having a diphenyl polymer mole percent of 5%, and a barrier layer of dimethyl-diphenyl silicone elastomer having a diphenyl polymer mole percent of 15%. Another suitable example of flexible shell that can be used according to the invention is a flexible shell including a substantially homogenous layer enveloping and in direct contact with the silicone gel of the core, made of a silicone elastomer comprising a polydimethylsiloxane backbone having diphenyl pendant groups such as the mole percent of said diphenyl siloxane units is about 15%.

The possibility to ever-more custom solutions to improve the sensory feel of the breast implant to match the feel of the natural flesh of the patient who will receive the breast is an important advantage and will improve the quality of life for patients and improve the emotional and social acceptance of such devices.

Another object of the invention concerns a process for additive manufacturing a 3D-shape article made of a customizable flesh simulating silicone gel or a customizable flesh simulating silicone foam, in particular for use in medical devices, comprising the steps of:
a) feeding into a first feed line the contents of the first package Part-A according to the invention and as defined above,
feeding into a second feed line the contents of the second package Part-B according to the invention and as defined above;
feeding into a third feed line the contents of the third package Part-C according to the invention and as defined above; and
eventually feeding into a fourth feed line the contents of the fourth package Part-D according to the invention and as defined above;
b) directing contents of said first feed line, said second feed line and said third feed line, and eventually said fourth feed line when present, into a mixing tank to yield a crosslinkable silicone composition X precursor of a silicone gel or a silicone foam,
c) printing with a 3D printer selected from an extrusion 3D printer or a material jetting 3D printer a portion of said crosslinkable silicone composition X to form a deposit into a matrix of a material SM1 which is a gel or microgel suitable for 3D-gel printing silicone gel or silicone foam, said deposit is achieved by way of a device which has at least one delivery unit which can be positioned in x-, y- and z-directions, d) allowing the printed crosslinkable silicone composition X to partially or totally crosslink, optionally by heating, to obtain a flesh simulating silicone gel deposit or a customizable flesh simulating silicone foam deposit within said matrix of the supportive material SM1, e) optionally repeating several times steps c) and d) until the desired 3D-shape is obtained, f) removing mechanically or via dissolution in a solvent said supporting material SM1, and g) recovering a 3D-shape article made of a customizable flesh simulating silicone gel or a customizable flesh simulating silicone foam, and wherein the sensory flesh-feel properties of the resulting silicone gel deposit or of the silicone foam deposit obtained in step d) are customized in step a) by metering the third feed line so as to add the required amounts of the contents of Part-C.

In step d), the curing of said crosslinkable silicone composition X in step b) of the process according to the invention can be easily obtained without the need of heat, so at ambient temperature 20° C. (+/−5° C.), by adjusting the level of inhibitor and/or catalyst. However, it can also be greatly accelerated by heat curing at a temperature range of between 80° C. to 200° C., preferably of between 100° C. to 185° C.

Printing is preferably carried out layer by layer with a 3D-printer. Advantageously the 3D printer is an extrusion 3D printer. 3D printing is generally associated with a host of related technologies used to fabricate physical objects from computer generated, e.g. computer-aided design (CAD), data sources. "3D printer" is defined as "a machine used for 3D printing" and "3D printing" is defined as "the fabrication of objects through the deposition of a material using a print head, nozzle, or another printer technology."

"Printing" is defined as depositing of a material, here a crosslinkable silicone composition X, using a print head, nozzle, or another printer technology. In this disclosure "3D or three-dimensional article, object or part" means an article, object or part obtained by additive manufacturing or 3D printing as disclosed above.

In general, all 3D printing processes have a common starting point, which is a computer-generated data source or program which may describe an object. The computer-generated data source or program can be based on an actual or virtual object. For example, an actual object can be scanned using a 3D scanner and scan data can be used to make the computer-generated data source or program. Alternatively, the computer-generated data source or program may be designed using a computer-aided design software. The computer-generated data source or program is typically converted into a standard tessellation language (STL) file format; however other file formats can also or additionally be used. The file is generally read via a 3D printing software, which takes over the file to separate it (or "cut it") into hundreds, thousands, or even millions of "slices." The 3D printing software typically outputs machine instructions, which may be in the form of G-code, which is read by the 3D printer to build each slice. The machine instructions are transferred to the 3D printer, which then builds the object, layer by layer, based on this slice information in the form of machine instructions. Thicknesses of these slices may vary.

An extrusion 3D printer is a 3D printer where the material is extruded through a nozzle, syringe or orifice during the manufacturing process. Material extrusion generally works by extruding material through a nozzle, syringe or orifice to print one cross-section of an object, which may be repeated for each subsequent layer. The extruded material bonds to the layer below it during cure of the material.

In one preferred embodiment, the method for manufacturing article made of silicone gels or silicone foam according to the invention uses an extrusion 3D printer. Crosslinkable silicone compositions X are extruded through a nozzle. The nozzle may be heated to aid in dispensing the addition crosslinking silicone composition.

The crosslinkable silicone composition X to be dispensed through the nozzle may be supplied from a cartridge-like system. It is also possible to use a coaxial three cartridges system with a static mixer and only one nozzle. Pressure will be adapted to the fluid to be dispensed, the associated nozzle average diameter and the printing speed. Because of the high shear rate occurring during the nozzle extrusion, the viscosity of the crosslinkable silicone compositions X is greatly lowered and so permits the printing of fine layers. Cartridge pressure could vary from 1 (atmospheric pressure) to 28 bars, preferably from 1 to 10 bars and most preferably from 2 to 8 bars. An adapted equipment using aluminum cartridges can be used to resist such a pressure. The nozzle and/or build platform moves in the x-y (horizontal plane) to complete the cross section of the object, before moving in the z-axis (vertical) plane once one layer is complete. The nozzle has a high x-y-z-movement precision around 10 µm. After each layer is printed in the x- and y-work plane, the nozzle is displaced in the z-direction only far enough that the next layer can be applied in the x-, y-work place. In this manner, the 3D article is built one layer at a time from the bottom to the upward.

The average diameter of a nozzle is related to the thickness of the layer. In an embodiment, the diameter of the layer is comprised from 50 to 2000 µm, preferably from 100 to 800 µm and most preferably from 100 to 500 µm. Advantageously, printing speed is comprised between 1 and 50 mm/s, preferably between 5 and 30 mm/s to obtain the best compromise between good accuracy and manufacture speed.

The said material SM1 is a gel or microgel suitable for 3D-gel printing silicone gel or silicone foam. The gel or microgel provides a constant support for the liquid material as it's being 3D-printed. Allowing to 3D-print in three dimensions. This allows more complex objects to be printed without the need for added supports, and at a faster pace.

Without to be bound by any theory, the said material SM1 acts as a constrained environment which enables to print low viscous non-crosslinked silicone composition X. Indeed, the gel or microgel applies a constant pressure to the non-crosslinked silicone composition X so as to allow enough time for the crosslinking reaction to occur during printing and to avoid any drop of the material. The pressure applied may be measured with a rheological characterization (shear stress in function of shear rate) using yield stress parameters Bingham fluid, the range of yield stress is preferably between 1 and 10 kPa.

In a preferred embodiment, said material SM1 is a sol-gel made from a composition containing water and a poloxamer which is non-compatible with the silicone gel or foam, i.e. there is no interpenetration between the poloxamer and the crosslinked silicone. This advantageously enables to obtain a good surface roughness of the silicone article manufactured, i.e. a roughness less than 100 nm. Moreover, the poloxamer is removed without polluting the silicone surface of the article.

As a most preferred embodiment, the supportive material SM1 is a sol-gel made from a composition comprising water and at least 20% by weight of at least one poloxamer such as a copolymer composed of poly(propylene oxide) and poly(ethylene oxide) blocks. The advantage of such the sol-gel is that it is self-healing. This advantageously allows a printing nozzle to repeatedly pass through the gel in the same area while the gel is simultaneously supporting the printed structure.

A poloxamer is a copolymer composed of poly(propylene oxide) (PO) and poly(ethylene oxide) (EO) block also named poly(propylene oxide) poly(ethylene oxide) block copolymer. Preferably, a poloxamer according to the invention is a triblock copolymer composed of a central PO block and two terminal EO block also named poly(ethylene oxide) poly(propylene oxide) poly(ethylene oxide) block copolymer, i.e the poloxamer according to the invention is preferably of the type EO-PO-EO triblock copolymer.

An advantageous feature of poloxamers is that they form gel with water in a sol-gel transition temperature process. At sol-gel transition temperature the rheological properties of a composition changes from a liquid-like state to a solid-like state. Aqueous solutions of poloxamers are liquid at low temperature and form a gel at higher temperature in a thermo-reversible process. The temperature at which the transition occurs in these systems depends on the poloxamer and its concentration. Therefore, by adjusting the concentrations of the aqueous composition of poloxamer, the temperature of the sol-gel transition will vary accordingly. Hence when the final step of the process according to the invention is reached, just by lowering the ambient temperature below said temperature of transition will make the supporting material to be in a liquid state so allowing to be removed smoothly just by washing with water.

Preferably, in the present invention, the aqueous poloxamer composition is solid at ambient temperature, i.e. at a temperature between 20 and 30° C. and liquid at lower temperature, i.e. at temperature below 15° C. Preferably, in the present invention, the poloxamer is composed of poly (propylene oxide) (PO) and poly(ethylene oxide) (EO) block. Preferably, the poloxamer of the invention is a triblock copolymer composed of a central PO block and two terminal EO blocks, and comprise from 25 to 90% by weight of EO units based on the total weight of the poloxamer, preferably from 30 to 80% by weight of EO units based on the total weight of the poloxamer, preferably from 50 to 75%, by weight of EO units based on the total weight of the poloxamer.

More preferably, the poloxamer according to the invention is a triblock copolymer composed of a central PO block and two terminal EO blocks for which the two EO blocks comprise each between 20 and 300 repeat units, preferably between 50 and 150 repeat units and the PO block comprises between 10 and 100 repeat units, preferably between 30 and 70 repeat units.

Advantageously, the poloxamer of the invention is a triblock copolymer composed of a central PO block and two terminal EO blocks with 70%+/−2% by weight of EO units. In a preferred embodiment, the poloxamer according to the invention is a triblock copolymer composed of a central PO block and two terminal EO blocks where the two EO blocks comprise each 100+/−10 repeat units and the PO block comprise 55+/−10 repeat units. Such poloxamer is for example sold under the name Pluronic F127® by BASF. Moreover, poloxamer and especially Pluronic F127® are biocompatible and thus can be used to prepare article for biological or medical uses.

Advantageously, the use of a poloxamer according to the invention enables to use water as a solvent in step f) of the process of the invention. This is of great interest especially for biological and medical uses of the articles obtained.

Another object of the invention, which is a variant of the previous claimed process, concerns a process for additive manufacturing a 3D-shape article made of a customizable flesh simulating silicone gel or a customizable flesh simulating silicone foam in particular for use in medical devices comprising the steps of:
a) feeding into a first feed line the contents of the first package Part-A according to the invention and as defined above,
    feeding into a second feed line the contents of the second package Part-B according to the invention and as defined above;
    feeding into a third feed line the contents of the third package Part-C according to the invention and as defined above; and
    eventually feeding into a fourth feed line the contents of the fourth package Part-D according to the invention and as described above;
b) directing contents of said first feed line, said second feed line and said third feed line, and eventually said fourth feed line when it is present, into a mixing tank to yield a non-crosslinked silicone composition X precursor of a silicone gel or a silicone foam,
c) printing with a 3D printer selected from an extrusion 3D printer or a material jetting 3D printer a portion of said non-crosslinked silicone composition X to form a deposit achieved by way of a device which has at least one delivery unit which can be positioned in x-, y- and z-directions onto a supportive material SM2 which is a gel or a microgel suitable for 3D printing silicone gel or silicone foam, and said supportive material SM2 is delivered simultaneously or at staggered intervals at a specific location by way of a device which has at least one delivery unit which can be positioned in x-, y- and z-directions,
d) allowing the printed non-crosslinked silicone composition X to partially or totally crosslink, optionally by heating, to obtain a flesh simulating silicone gel deposit or a customizable flesh simulating silicone foam deposit onto said supportive material SM2,
e) optionally repeating several times steps c) and d) onto the same supportive material SM2 or onto another supportive material SM2 delivered as in step c) until the desired 3D-shape is obtained,
f) removing mechanically or via dissolution in a solvent said supporting material SM2, and
g) recovering a 3D-shape article made of a customizable flesh simulating silicone gel or a customizable flesh simulating silicone foam, and
wherein the sensory flesh-feel properties of the resulting silicone gel deposit or of the silicone foam deposit obtained in step d) are customized in step a) by metering the third feed line so as to add the required amounts of the contents of Part-C.

Any suitable supportive material useful for 3D-printed silicone gels or foam can be used. As a preferred embodiment the supporting material SM2 has the same definition as the supportive material SM1 which is fully described above.

All the described different embodiments of the previous claimed process also apply for this claimed process.

Another object of the invention concerns a device in particular an implant comprising a customizable flesh simulating silicone gel or a customizable flesh simulating silicone foam according to the invention and as described above.

Another object of the invention concerns a 3D-shape article made of a customizable flesh simulating silicone gel or a customizable flesh simulating silicone foam manufactured according to the additive manufacturing processes of the invention and as described above.

In a preferred embodiment said 3D-shape article, made of a customizable flesh simulating silicone foam manufactured according to the additive manufacturing processes of the invention and as described above, is a scaffold for tissue regeneration applications.

Another object of the invention concerns a medical implant comprising a 3D-shape article according to the invention and as described above.

Optionally, the resulting 3D-shape articles may be subjected to different post-processing regimes. In an embodiment, the method further comprises the step of heating the three-dimensional silicone article. Heating can be used to expedite cure.

The present invention will now be disclosed by means of the following non-limiting examples.

EXAMPLES

1) Test Methods a) Resilience

Equipment: Shore Resiliometer, Model SR-1.

Specimen Preparation: Gel specimen were prepared by curing 29 grams in an aluminum weigh dish at 120° C. for 30 min. LSR specimen were cured as slabs 177° C. for 5 min and stacked 3 slabs high.

Test Conditions: Room temperature (23° C., +/−2° C.). 400 mm Drop height+/−1 mm. Stainless steel plunger type 303 with a mass of 28 g (+/−0.5 g).

Procedure: The guide rod is raised and the aluminum dish containing sample or stack of slabs is placed underneath. The guide rod is let come to rest on top of sample. Release The plunger is released from locked in top positions 3 times to ensure a clean drop. The initial bounce is recorded and the test is repeated three times b) Penetration Equipment: Penetrometer: KIC with 0.25" diameter foot, ID #008-01. Specimen Preparation: 55 g of Part-A and 55 g of combined Part-B and Part-C were mixed in a speed mixer cup (frequency 3,000 rpm for 15 seconds). After being mixed the material was poured into a Falcon penetration jars and then deaired. The penetration cup was cured at 120° C. for 30 minutes.

Test Conditions: Room temperature (23° C.+/−2° C.). Flat end 0.25" diameter foot probe Procedure: The probe is guided down until it barely touches the surface of the gel and lock it in place. The probe is then released so that it drops freely for 10 seconds. It is recorded how many mm the probe dropped. The test is repeated 3 times in different spots the average is registered.

c) Hardness

Shore A is measured according to ASTM-2240 standard.

2) Raw Materials

Organopolysiloxane A1-1=polydimethylsiloxane with dimethylvinylsilyl end-units with a viscosity at 25° C. of about 100 mPa·s;

Organopolysiloxane A1-2=polydimethylsiloxane with dimethylvinylsilyl end-units with a viscosity at 25° C. of about 600 mPa·s;

Organopolysiloxane A1-3=polydimethylsiloxane with dimethylvinylsilyl end-units with a viscosity at 25° C. of about 1500 mPa·s;

Organopolysiloxane A1-4=polydimethylsiloxane with dimethylvinylsilyl end-units with a viscosity at 25° C. of about 4,000 mPa·s;

Organopolysiloxane A1-5=polydimethylsiloxane with dimethylvinylsilyl end-units with a viscosity at 25° C. of about 10,000 mPa·s;

Organopolysiloxane A1-6=polydimethylsiloxane with dimethylvinylsilyl end-units with a viscosity at 25° C. of about 20,000 mPa·s;

Organopolysiloxane A1-7=polydimethylsiloxane with dimethylvinylsilyl end-units with a viscosity at 25° C. of about 60,000 mPa·s;

Organopolysiloxane A1-8=polydimethylsiloxane with dimethylvinylsilyl end-units with a viscosity at 25° C. of about 100,000 mPa·s;

Organopolysiloxane A1-9=polydimethylsiloxane with 2 methylvinylsilyl siloxy units (in the chain) with a viscosity at 25° C. of about 600 mPa·s;

Organopolysiloxane B1-1=poly(methylhydrogeno)(dimethyl)siloxane with SiH groups in-chain and end-chain ($\alpha/\omega$) with a viscosity at 25° C. ranging from 200 mPa·s to 350 mPa·s, and having in average from 15 to 17 SiH reactive groups and from 135 to 137 dimethylsiloxy units;

Polydimethylsiloxane D1-1 with a viscosity at 25° C. of about 350 mPa·s;

Polydimethylsiloxane D1-2 with a viscosity at 25° C. of about 1,000 mPa·s;

Polydimethylsiloxane D1-3 with a viscosity at 25° C. of about 5,000 mPa·s

Polydimethylsiloxane D1-4 with a viscosity at 25° C. of about 30,000 mPa·s;

Polydimethylsiloxane D1-5 with a viscosity at 25° C. of about 60,000 mPa·s;

Catalyst C1-1=10% by weight of Platinum metal, known as Karstedt's catalyst diluted in a in 350 cS dimethylvinyldimer, sold by Johnson Matthey Company;

Cure rate controller G1-1=1-Ethynyl-1-cyclohexanol (ECH)

[SiH/Si-vinyl]=molar ratio of silicon-bonded hydrogen atoms contained in components B1-x and B2-x to alkenyl groups contained in components A1-x and A2-x;

SILBIONE® LSR 4301 Part A & B: two-component platinum-catalyzed silicone sold by Elkem Silicone.

SILBIONE® LSR 4305 Part A & B: two-component platinum-catalyzed silicone sold by Elkem Silicone.

SILBIONE® LSR 4310 Part A & B: two-component platinum-catalyzed silicone sold by Elkem Silicone.

SILBIONE® LSR 4325 Part A & B: two-component platinum-catalyzed silicone sold by Elkem Silicone.

SILBIONE® LSR 4350 Part A & B: two-component platinum-catalyzed silicone sold by Elkem Silicone.

3) Preparation of Silicone Gels

Different 3 or 4 part-kit formulations are prepared (Part-A, Part-B, Part-C and Part-D) are prepared separately and the contents are quoted in Tables 1 to 11

TABLE 1

Kit for preparing crosslinkable silicone composition 1 (comparative).

| | % by weight | [SiH/Si-vinyl] |
|---|---|---|
| Components of package Part-A | | |
| Organopolysiloxane A1-3 | 99.998 | 1.10 |
| Catalyst C1-1 | 0.002 | |
| Components of packages Part-B and Part-C | | |
| Organopolysiloxane B1-1 (in Part-B) | 6.520 | |
| Cure rate controller G1-1 (in Part-B) | 0.005 | |
| Polydimethylsiloxane D1-1 (in Part-C) | 93.475 | |

TABLE 2

Kit for preparing crosslinkable silicone composition 2 (comparative).

| | % by weight | [SiH/Si-vinyl] |
|---|---|---|
| Components of package Part-A | | |
| Organopolysiloxane A1-3 | 99.998 | 1.20 |
| Catalyst C1-1 | 0.002 | |
| Components of packages Part-B and Part-C | | |
| Organopolysiloxane B1-1 (in Part-B) | 7.110 | |
| Cure rate controller G1-1 (in Part-B) | 0.005 | |
| Polydimethylsiloxane D1-1 (in Part-C) | 92.885 | |

TABLE 3

Kit for preparing crosslinkable silicone composition 3 (comparative).

| | % by weight | [SiH/Si-vinyl] |
|---|---|---|
| Components of package Part-A | | |
| Organopolysiloxane A1-7 | 99.998 | 2.27 |
| Catalyst C1-1 | 0.002 | |
| Components of packages Part-B and Part-C | | |
| Organopolysiloxane B1-1 (in Part-B) | 4.150 | |
| Cure rate controller G1-1 (in Part-B) | 0.005 | |
| Polydimethylsiloxane D1-5 (in Part-C) | 95.845 | |

TABLE 4

Kit for preparing crosslinkable silicone composition 4 (Invention).

| | % by weight | [SiH/Si-vinyl] |
|---|---|---|
| Components of package Part-A | | |
| Organopolysiloxane A1-1 | 99.998 | 0.34 |
| Catalyst C1-1 | 0.002 | |
| Components of packages Part-B and Part-C | | |
| Organopolysiloxane B1-1 (in Part-B) | 8.500 | |
| Cure rate controller G1-1 (in Part-B) | 0.005 | |
| Polydimethylsiloxane D1-1 (in Part-C) | 91.495 | |

TABLE 5

Kit for preparing crosslinkable silicone composition 5 (Invention).

| | % by weight | [SiH/Si-vinyl] |
|---|---|---|
| Components of package Part-A | | |
| Organopolysiloxane A1-2 | 99.998 | 0.35 |
| Catalyst C1-1 | 0.002 | |
| Components of packages Part-B and Part-C | | |
| Organopolysiloxane B1-1 (in Part-B) | 3.000 | |
| Cure rate controller G1-1 (in Part-B) | 0.005 | |
| Polydimethylsiloxane D1-2 (in Part-C) | 96.995 | |

TABLE 6

Kit for preparing crosslinkable silicone composition 6 (Invention).

| | % by weight | [SiH/Si-vinyl] |
|---|---|---|
| Components of package Part-A | | |
| Organopolysiloxane A1-9 | 99.998 | 0.35 |
| Catalyst C1-1 | 0.002 | |
| Components of packages Part-B and Part-C | | |
| Organopolysiloxane B1-1 (in Part-B) | 3.000 | |
| Cure rate controller G1-1 (in Part-B) | 0.005 | |
| Polydimethylsiloxane D1-2 (in Part-C) | 96.995 | |

TABLE 7

Kit for preparing crosslinkable silicone composition 7 (Invention).

| | % by weight | [SiH/Si-vinyl] |
|---|---|---|
| Components of package Part-A | | |
| Organopolysiloxane A1-4 | 99.998 | 0.34 |
| Catalyst C1-1 | 0.002 | |
| Components of packages Part-B and Part-C | | |
| Organopolysiloxane B1-1 (in Part-B) | 1.370 | |
| Cure rate controller G1-1 (in Part-B) | 0.005 | |
| Polydimethylsiloxane D1-3 (in Part-C) | 98.625 | |

TABLE 8

Kit for preparing crosslinkable silicone composition 8 (Invention).

|  | % by weight | [SiH/Si-vinyl] |
|---|---|---|
| Components of package Part-A | | |
| Organopolysiloxane A1-6 | 99.998 | 0.34 |
| Catalyst C1-1 | 0.002 | |
| Components of packages Part-B and Part-C | | |
| Organopolysiloxane B1-1 (in Part-B) | 0.860 | |
| Cure rate controller G1-1 (in Part-B) | 0.005 | |
| Polydimethylsiloxane D1-4 (in Part-C) | 99.135 | |

TABLE 9

Kit for preparing crosslinkable silicone composition 9 (Invention).

|  | % by weight | [SiH/Si-vinyl] |
|---|---|---|
| Components of package Part-A | | |
| Organopolysiloxane A1-8 | 99.998 | 0.34 |
| Catalyst C1-1 | 0.002 | |
| Components of packages Part-B and Part-C | | |
| Organopolysiloxane B1-1 (in Part-B) | 0.550 | |
| Cure rate controller G1-1 (in Part-B) | 0.005 | |
| Polydimethylsiloxane D1-5 (in Part-C) | 99.445 | |

TABLE 10

Kit for preparing crosslinkable silicone composition 10 (Invention).

|  | % by weight | [SiH/Si-vinyl] |
|---|---|---|
| Components of package Part-A | | |
| Organopolysiloxane A1-7 | 99.998 | 0.30 |
| Catalyst C1-1 | 0.002 | |
| Components of packages Part-B and Part-C | | |
| Organopolysiloxane B1-1 (in Part-B) | 0.550 | |
| Cure rate controller G1-1 (in Part-B) | 0.005 | |
| Polydimethylsiloxane D1-5 (in Part-C) | 99.445 | |

TABLE 11

Kit for preparing crosslinkable silicone composition 11 (Invention).

|  | % by weight | [SiH/Si-vinyl] |
|---|---|---|
| Components of package Part-A | | |
| Organopolysiloxane A1-3 | 99.998 | 0.32 |
| Catalyst C1-1 | 0.002 | |
| Components of packages Part-B and Part-C | | |
| Organopolysiloxane B1-1 (in Part-B) | 1.905 | |
| Cure rate controller G1-1 (in Part-B) | 0.005 | |
| Polydimethylsiloxane D1-1 (in Part-C) | 98.090 | |

3) Preparation of Gels

All the parts are mixed so that the crosslinking occurred at 120° C. for 30 minutes. Physical properties are recorded in the following table 12.

TABLE 12

Physical properties of the cured formulations.

| Compositions | Molar ration [SiH/Si-vinyl] | Penetration of the cured product (mm) | Durometer (Shore 00) | Hardness, Shore A | Physical state | Resilience 29 g/120° C./30 min |
|---|---|---|---|---|---|---|
| Composition 1 (comparative) | 1.10 | 0.20 | 45.6 | — | elastomer like | 57 |
| Composition 2 (comparative) | 1.20 | 0.20 | 37.3 | — | elastomer like | 38 |
| Composition 3 (comparative) | 2.27 | 0.30 | 30 | — | elastomer like | 22 |
| Composition 4 (invention) | 0.31 | 4.10 | — | — | gel | No bounce |
| Composition 5 (invention) | 0.35 | 13.13 | — | — | gel | No bounce |
| Composition 6 (invention) | 0.35 | 11.13 | — | — | gel | No bounce |
| Composition 7 (invention) | 0.34 | 13.27 | — | — | gel | No bounce |
| Composition 8 (invention) | 0.34 | 23.53 | — | — | gel | No bounce |
| Composition 9 LSR-4301 (comparative) | — | elastomer | — | 1 | Elastomer like | 20 |
| Composition 10 LSR-4305 (comparative) | — | elastomer | — | 5 | Elastomer like | 21 |
| Composition 11 LSR-4310 (comparative) | — | elastomer | — | 10 | Elastomer like | 33 |

TABLE 12-continued

Physical properties of the cured formulations.

| Compositions | Molar ration [SiH/Si-vinyl] | Penetration of the cured product (mm) | Durometer (Shore 00) | Hardness, Shore A | Physical state | Resilience 29 g/120° C./30 min |
|---|---|---|---|---|---|---|
| Composition 12 LSR-4325 (comparative) | — | elastomer | — | 23 | Elastomer like | 34 |
| Composition 13 LSR-4350 (comparative) | — | elastomer | — | 50 | Elastomer like | 51 |

As can be seen in Table 12, the 3 kit-part formulations according to the invention give, when mixed and cured, silicone gels which have the required resilience properties (no bounce). Furthermore, compositions 4 to 8 were also evaluated by a panel of experts skilled in the art which concluded to a verified flesh feel sensory and also to a variation of perception of the flesh-like properties of the cured gels.

4) Preparation of a Silicone Foam According to the Invention

All the ingredients of the 4-parts kit which are described in Table 14 are mixed and temperature is maintained at 150° C. for 30 minutes so that the crosslinking occurred. Physical properties are recorded in Table 15.

TABLE 14

Kit for preparing crosslinkable silicone composition 14 precursor of a silicone foam (Invention).

| | % by weight | Amount (g) |
|---|---|---|
| Components of package Part-A | | |
| Organopolysiloxane A1-5 | 99.98 | 72.000 |
| Catalyst C1-1 | 0.02 | 0.015 |
| Components of packages Part-B | | |
| Organopolysiloxane A1-5 | 98.08 | 73.58 |
| Cure rate controller G1-1 (in Part-B) | 0.01 | 0.008 |
| Organopolysiloxane B1-1 | 1.91 | 1.43 |
| Components of packages Part-C | | |
| Polydimethylsiloxane D1-1 | 100 | 49.00 |
| Components of packages Part-D | | |
| Organopolysiloxane A1-5 | 50 | 2.0 |
| Ammonium Bicarbonate | 50 | 2.0 |

TABLE 15 properties of the silicone composition 14 (Invention) before and after crosslinking reaction.

| [SiH/Si-vinyl] | 0.31 |
|---|---|
| Viscosity of total system (Part-A, Part-B, Part-C and Part-D mixed together (before crosslinking) | 5,000 mPa•s |
| Density of the silicone foam | 0.6 |
| Resilience of the silicone foam | No bounce |

The invention claimed is:

1. A kit for preparing a customizable flesh simulating silicone gel comprising:

a first package Part-A comprising a mixture of:
  i) 5 to 95 parts by weight of at least one organopolysiloxane A1 having at least two alkenyl groups bonded to silicon per molecule, said alkenyl groups each containing from 2 to 14 carbon atoms, and
  ii) at least one hydrosilylation catalyst C1;
a second package Part-B comprising a mixture of:
  i) 95 to 5 parts by weight of at least one organopolysiloxane A2 having at least two alkenyl groups bonded to silicon per molecule, said alkenyl groups each containing from 2 to 14 carbon atoms,
  ii) at least one organosilicon compound B1 having at least two hydrogen atoms bonded to silicon per molecule,
  iii) optionally at least one diorganohydrogensiloxy-terminated polyorganosiloxane as a chain extender B2, and
  iv) optionally a cure rate controller G1 which slows the curing rate, and
a third package Part-C comprising:
  i) at least one linear polydimethylsiloxane D1 which has a dynamic viscosity at 25° C. of between 50 mPa·s and 100000 mPa·s,
  ii) optionally at least one organopolysiloxane A1 or A2, and
  iii) optionally at least one additive H1
with the proviso that:
  e) the amounts of components A1 and A2 is 100 parts by weight when the contents of the three packages Part-A, Part-B and Part-C are combined,
  f) the components B1 and B2 are present in an amount such that the molar ratio of silicon-bonded hydrogen atoms contained in components B1 and B2 to alkenyl groups contained in components A1 and A2 ranges from 0.25 to 0.90;
  g) the amount of component D1 is at least about 0.1 part by weight percent to about 90 parts by weight for each 100 parts of the combined components A1 and A2 when the contents of the three packages Part-A, Part-B and Part-C are combined, and
  h) the component C1 is present in an amount sufficient to cure the composition formed when the contents of the three packages Part-A, Part-B and Part-C are combined.

2. A kit according to claim 1, wherein the linear polydimethylsiloxane D1 has the following formula:

in which is an integer from 50 to 900.

3. A kit according to claim 1, further comprising a fourth package Part-D, wherein the package Part-D comprises;
at least one blowing agent E1,
and
optionally the at least one organopolysiloxane A1 or A2.

4. A kit according to claim 1, wherein the third package Part-C further comprises at least one blowing agent E1.

5. A kit according to claim 3, wherein the blowing agent E1 is selected from the group consisting of ammonium bicarbonate, ammonium hydrogen carbonate, alkali metal hydrogen carbonate and mixtures thereof, and wherein the blowing agent E1 has particles having a median particle size (D50) of ≤50 µm.

6. A kit according to claim 1, wherein said organosilicon compound B1 is an organopolysiloxane comprising:
at least three siloxy units of formula (XL-1):

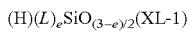

$(H)(L)_e SiO_{(3-e)/2}$ (XL-1)

in which the symbol H represents a hydrogen atom, the symbol L represents an alkyl having from 1 to 8 carbon atoms inclusive or a C6 to $C_{10}$ aryl, and the symbol e is equal to 0, 1 or 2; and
optionally other siloxy units of formula (XL-2):

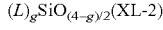

$(L)_g SiO_{(4-g)/2}$ (XL-2)

in which the symbol L represents an alkyl having from 1 to 8 carbon atoms inclusive or a $C_6$ to $C_{10}$ aryl, and the symbol g is equal to 0, 1, 2 or 3.

7. A kit according to claim 1, wherein:
the organopolysiloxanes A1 and A2 have a dynamic viscosity at 25° C. of between 100 mPa·s and 120000 mPa·s, and
the chain extender B2 is present and has a dynamic viscosity at 25° C. of between 1 mPa·s and 500 mPa·s, and
the organosilicon compound B1 has a dynamic viscosity at 25° C. of between 5 mPa·s and 2000 mPa·s.

8. A kit according to claim 1, wherein the packages Part-A, Part-B and/or Part-C further comprise at least one thixotropic agent F1 and optionally at least one organopolysiloxanepolyoxyalkylene copolymer.

9. A process for preparing a customizable flesh simulating silicone gel or a customizable flesh simulating silicone foam comprising:
a) combining the contents or portions of the three packages Part-A, Part-B and Part-C, according to claim 1 to yield a crosslinkable silicone composition X precursor of a silicone gel or a silicone foam, and
b) allowing the crosslinkable silicone composition X to crosslink, to yield a customizable flesh simulating silicone gel or a customizable flesh simulating silicone foam, and
wherein sensory flesh-feel properties of the resulting silicone gel or the silicone foam are customized in a) by metering and adding the required amounts of the contents of Part-C corresponding to the required level of sensory flesh-feel properties of the customizable flesh simulating silicone gel or of the customizable flesh simulating silicone foam.

10. A customizable flesh simulating silicone gel or a customizable flesh simulating silicone foam obtained from a process according to claim 9.

11. A breast implant comprising a shell and a filling enclosed by a shell, wherein the filling is the customizable flesh simulating silicone gel or the customizable flesh simulating silicone foam of claim 10.

12. A device comprising a customizable flesh simulating silicone gel or a customizable flesh simulating silicone foam according to claim 10.

13. A process for additive manufacturing a 3D-shape article made of a customizable flesh simulating silicone gel or a customizable flesh simulating silicone foam, the process comprising:
a) feeding into a first feed line contents of the first package Part-A according to claim 1,
feeding into a second feed line contents of the second package Part-B according to claim 1;
feeding into a third feed line contents of the third package Part-C according to claim 1; and
optionally feeding into a fourth feed line contents of a fourth package Part-D comprising at least one blowing agent E1 and optionally the at least one organopolysiloxane A1 or A2 according to claim 1;
b) directing contents of said first feed line, said second feed line and said third feed line, and said fourth feed line when present, into a mixing tank to yield a crosslinkable silicone composition X precursor of a silicone gel or a silicone foam,
c) printing with a 3D printer selected from an extrusion 3D printer or a material jetting 3D printer a portion of said crosslinkable silicone composition X to form a deposit into a matrix of a supporting material SM1 which is a gel or microgel suitable for 3D-gel printing silicone gel or silicone foam, said deposit is achieved by way of a device which has at least one delivery unit which can be positioned in x-, y- and z-directions,
d) allowing the printed crosslinkable silicone composition X to partially or totally crosslink, optionally by heating, to obtain a flesh simulating silicone gel deposit or a customizable flesh simulating silicone foam deposit within said matrix of the supportive material SM1,
e) optionally repeating c) and d) one or more times until the desired 3D-shape is obtained,
f) removing said supporting material SM1 mechanically or via dissolution in a solvent, and
g) recovering the 3D-shape article made of a customizable flesh simulating silicone gel or a customizable flesh simulating silicone foam, and
wherein sensory flesh-feel properties of the resulting silicone gel deposit or of the silicone foam deposit obtained in d) are customized in a) by metering the third feed line so as to add the required amounts of the contents of Part-C.

14. A process for additive manufacturing a 3D-shape article made of a customizable flesh simulating silicone gel or a customizable flesh simulating silicone foam, the process comprising:
a) feeding into a first feed line contents of the first package Part-A according to claim 1,
feeding into a second feed line contents of the second package Part-B according to claim 1,
feeding into a third feed line contents of the third package Part-C according to claim 1; and
optionally feeding into a fourth feed line the contents of a fourth package Part-D comprising at least one blowing agent E1 and optionally the at least one organopolysiloxane A1 or A2 according to claim 1,
b) directing contents of said first feed line, said second feed line and said third feed line, and said fourth feed line when it is present, into a mixing tank to yield a crosslinkable silicone composition X precursor of a silicone gel or a silicone foam, c) printing with a 3D printer selected from an extrusion 3D printer or a material jetting 3D printer a portion of said crosslinkable silicone composition X to form a deposit achieved by way of a device which has at least one delivery unit which can be positioned in x-, y- and z-directions onto a supportive material SM2, and said supportive material SM2 is delivered simultaneously or at staggered intervals at a specific location by way of a device which has at least one delivery unit which can be positioned in x-, y- and z-directions, d) allowing the printed crosslinkable silicone composition X to partially or totally crosslink, optionally by heating, to obtain a flesh simulating silicone gel deposit or a customizable flesh simulating silicone foam deposit onto said supportive material SM2, e) optionally repeating c) and d) one or more times onto the same supportive material SM2 or onto another supportive material SM2 delivered as in c) until the desired 3D-shape is obtained, f) removing said supporting material SM2 mechanically or via dissolution in a solvent, and g) recovering the 3D-shape article made of a customizable flesh simulating silicone gel or a customizable flesh simulating silicone foam, and wherein sensory flesh-feel properties of the resulting silicone gel deposit or of the silicone foam deposit obtained in d) are customized in a) by metering the third feed line so as to add the required amounts of the contents of Part-C.

15. A 3D-shape article made of a customizable flesh simulating silicone gel or a customizable flesh simulating silicone foam manufactured by a process according to claim 13.

16. A 3D-shape article made of a customizable flesh simulating silicone foam manufactured by a process according to claim 13 which is a scaffold for tissue regeneration applications.

17. A medical implant comprising a 3D-shape article according to claim 16.

* * * * *